(12) United States Patent
Dayal

(10) Patent No.: US 8,442,842 B2
(45) Date of Patent: May 14, 2013

(54) PHARMACEUTICAL CLEARINGHOUSE FOR INSTITUTIONS

(76) Inventor: Sandeep Dayal, Long Grove, IL (US)

( * ) Notice: Subject to any disclaimer, the term of this patent is extended or adjusted under 35 U.S.C. 154(b) by 581 days.

(21) Appl. No.: 11/695,331

(22) Filed: Apr. 2, 2007

(65) Prior Publication Data

US 2007/0233522 A1    Oct. 4, 2007

Related U.S. Application Data

(60) Provisional application No. 60/744,841, filed on Apr. 14, 2006, provisional application No. 60/744,029, filed on Mar. 31, 2006.

(51) Int. Cl.
*G06Q 50/00* (2012.01)
(52) U.S. Cl.
USPC .................................................. 705/2; 705/3
(58) Field of Classification Search .................. 705/2, 3, 705/4
See application file for complete search history.

(56) References Cited

U.S. PATENT DOCUMENTS

| 6,804,787 | B2 * | 10/2004 | Dick ................................ 726/1 |
| 6,879,959 | B1 * | 4/2005 | Chapman et al. ................. 705/2 |
| 2002/0128860 | A1 | 9/2002 | Leveque et al. |
| 2003/0055727 | A1 | 3/2003 | Walker et al. |
| 2004/0236607 | A1 * | 11/2004 | Kost et al. ......................... 705/2 |
| 2005/0015277 | A1 * | 1/2005 | Mau ................................ 705/2 |
| 2005/0240473 | A1 * | 10/2005 | Ayers et al. ..................... 705/14 |

OTHER PUBLICATIONS

Harmon, et al., "Outpatient Medication Assistance Program in a Rural Setting: The Central Louisiana Medication Access Program", American Journal of Health-System Pharmacy, 2004; 61(6), http://www.medscape.com/viewarticle/472700_3.

* cited by examiner

*Primary Examiner* — Gerald J. O'Connor
*Assistant Examiner* — Edward Winston, III
(74) *Attorney, Agent, or Firm* — Onello & Mello, LLP

(57) ABSTRACT

A pharmaceutical clearinghouse establishes relationships with a network of FNA Agents servicing requests from patients under institutional patient assistance programs, and with a network of pharmaceutical providers. In response to the clearinghouse receiving a patient request for a pharmaceutical from an FNA Agent, the clearinghouse obtains a subsidy from at least one in-network pharmaceutical provider and provides the subsidy to the FNA Agent; the subsidy may be cash, in-kind pharmaceutical or a combination thereof.

30 Claims, 7 Drawing Sheets

| Market Share | | 10% | 20% | 30% | 40% | 50% | 60% | 70% | 80% | 90% | 100% |
|---|---|---|---|---|---|---|---|---|---|---|---|
| Variable Contribution | $ | (3,256) $ | (2,581) $ | (1,906) $ | (1,231) $ | (556) $ | 119 $ | 794 $ | 1,469 $ | 2,144 $ | 2,819 |
| Revenue transferred to competitior | $ | 10,800 $ | 9,600 $ | 8,400 $ | 7,200 $ | 6,000 $ | 4,800 $ | 3,600 $ | 2,400 $ | 1,200 $ | • |

Pharmaceutical Drug Manufacturer Economics on PAP -- Typical Biologic Drug

|  | Market Share | | Market Share Adjusted |
|---|---|---|---|
|  |  |  | 30% |
| Revenue | | | |
| Revenue at retail price of drug[1] | | $ 15,000 | $ 4,500 |
| Revenues lost to lack of full regimen compliance[2] | 20% | $ (3,000) | $ (900) |
| Net revenue | | $ 12,000 | $ 3,600 |
| Variable Costs | | | |
| Distribution costs[3] | 10.0% | $ 1,500 | $ 450 |
| Costs of Goods Sold[3] | 12.5% | $ 1,875 | $ 563 |
| Royalties[3] | 12.5% | $ 1,875 | $ 563 |
| Average co-pay subsidy at payout rate[4] | 80.0% | $ 4,095 | $ 3,276 |
| Foundation administrative costs[5] | 20.0% | $ 819 | $ 655 |
| Net variable costs | | | $ 5,506 |
| Net Contribution | | | $ (1,906) |

*Notes*
[1] Retail revenues assume full-year use at indicated dosage. Market share adjusted revenues are retail revenues multiplied by market share
[2] Patients do not fully comply with the prescribed dosage levels or extend the time between dosages
[3] Costs allocated in proportion to share since only in those cases manufacturer drug is used
[4] Average patient assumed to receive 80% of the maximum possible co-pay under standard Part D benefit and paid for all brands
[5] Foundation costs of 20% of disbursed funds are typical -- and apply to funds towards manufacturer and competing brands

FIG. 1 *(Prior Art)*

| Market Share | 10% | 20% | 30% | 40% | 50% | 60% | 70% | 80% | 90% | 100% |
|---|---|---|---|---|---|---|---|---|---|---|
| Variable Contribution | $ (3,256) | $ (2,581) | $ (1,906) | $ (1,231) | $ (556) | $ 119 | $ 794 | $ 1,469 | $ 2,144 | $ 2,819 |
| Revenue transferred to competitor | $ 10,800 | $ 9,600 | $ 8,400 | $ 7,200 | $ 6,000 | $ 4,800 | $ 3,600 | $ 2,400 | $ 1,200 | $ - |

FIG. 2

| Clearinghouse Model Illustration – 2 Branded + 1 Low Cost | | | | | |
|---|---|---|---|---|---|
| Patients | ... On Brand X | ... On Brand Y | ... On Brand Z | Totals | Disbursements |
| FNA Agent A | 50 | 200 | 25 | 275 | $ 600,000 |
| FNA Agent B | 250 | 500 | 25 | 775 | $ 1,850,000 |
| FNA Agent C | 250 | 250 | 50 | 550 | $ 1,575,000 |
| FNA Agent D | 50 | 50 | 300 | 400 | $ 1,475,000 |
| Total | 600 | 1,000 | 400 | 2,000 | $ 5,500,000 |
| Share of patients (market share) | 30% | 50% | 20% | 100% | |
| Retail Price of Drug | $15,000 | $3,500 | $15,000 | | |
| Average Assistance provided (incl. FNA Agent costs) | $4,000 | $1,500 | $4,000 | | |
| Brands participating in assistance | Yes | No | Yes | | |
| Total funding needed | $2,400,000 | $1,500,000 | $1,600,000 | $5,500,000 | |
| Funding needed for to cover participant brands only | $ 2,400,000 | $ - | 1,600,000 | $4,000,000 | |
| Ratio of total vs. participant brand required assistance | | | | 138% | |
| Payments to Clearinghouse | $3,300,000 | $0 | $2,200,000 | $5,500,000 | |
| Funding applied toward contributing brand | 73% | N/A | 73% | | |
| Price after distribution margin (10%) | $ 13,500 | $ 3,150 | 13,500 | | |
| Effective assistance per patient | $ 5,500 | $ - | 5,500 | | |
| Effective discount on drug | 41% | 0% | 41% | | |

FIG. 4

Clearinghouse Model Illustration – Low Cost Drug Preference

| Patients | ... On Brand X | ... On Brand Y | ... On Brand Z | Totals | Disbursements |
|---|---|---|---|---|---|
| FNA Agent A | 50 | 200 | 25 | 275 | $ 600,000 |
| FNA Agent B | 250 | 500 | 25 | 775 | $ 1,850,000 |
| FNA Agent C | 250 | 250 | 50 | 550 | $ 1,575,000 |
| FNA Agent D | 50 | 50 | 300 | 400 | $ 1,475,000 |
| Total | 600 | 1,000 | 400 | 2,000 | $ 5,500,000 |
| Share of patients (market share) | 30% | 50% | 20% | 100% | |
| Retail Price of Drug | $15,000 | $3,500 | $15,000 | | |
| Average Assistance provided (incl. FNA Agent costs) | $4,000 | $1,500 | $4,000 | | |
| Brands participating in assistance | Yes | Yes | No | | |
| Total funding needed | $2,400,000 | $1,500,000 | $1,600,000 | $5,500,000 | |
| Funding needed for to cover participant brands only | $ 2,400,000 | $ 1,500,000 | - | $3,900,000 | |
| Ratio of total vs. participant brand required assistance | | | | 141% | |
| Payments to Clearinghouse | $4,000,000 | 1,500,000 | $0 | $5,500,000 | |
| Funding applied toward contributing brand | 60% | 100% | N/A | | |
| Price after distribution margin (10%) | $ 13,500 | $ 3,150 | 13,500 | | |
| Effective assistance per patient | $ 6,667 | $ 1,500 | - | | |
| Effective discount on drug | 49% | 43% | 0% | | |

*FIG. 5*

PHARMACEUTICAL CLEARINGHOUSE FOR INSTITUTIONS

CROSS REFERENCE TO RELATED APPLICATIONS

This application claims the benefit under 35 U.S.C. §119 (e) of U.S. Provisional Application No. 60/744,841, filed Apr. 14, 2006, entitled PHARMACEUTICAL CLEARINGHOUSE FOR INSTITUTIONS and U.S. Provisional Application No. 60/744,029, filed Mar. 31, 2006, entitled PHARMACEUTICAL CLEARINGHOUSE METHOD AND SYSTEM.

This application may also be related to U.S. application Ser. No. 11/692,639, entitled PHARMACEUTICAL CLEARINGHOUSE METHOD AND SYSTEM, filed Mar. 28, 2007, which claimed the benefit under 35 U.S.C. §119(e) of U.S. Provisional Application No. 60/744,029, filed Mar. 31, 2006, entitled PHARMACEUTICAL CLEARINGHOUSE METHOD AND SYSTEM.

FIELD OF INTEREST

The present inventive concepts relate to the field of pharmaceuticals, and more specifically to systems and methods for distributing pharmaceutical subsidies to patients via independent Financial Need Assessment Agents or institutions.

BACKGROUND

Two segments of patients require some form of subsidy or assistance in accessing prescription drugs or other treatments. Pharmaceutical provider, such as drug manufacturers, assist indigent, uninsured patients typically by providing them with free drug. They assist low income (but not necessarily indigent), under-insured patients indirectly through drug discounts in one form or another. In the case of Medicare and Medicaid patients, anti-kick back statutes and civil monetary penalties can be implicated if these programs are not properly structured. The Office of Inspector General (OIG) is the branch of the United States government charged with oversight over such matters.

Medicare launched the Part D prescription drug plan (PDP) on Jan. 1, 2006. Up to thirty million Americans were anticipated to sign up for Part D coverage by the end of 2006, and likely more later. The Part D prescription drug plan is designed to encourage patients to seek out lower cost drugs and therapeutic alternatives. The program typically requires the patient to cover the first $250 of prescription drug costs themselves, pays 75% of the amount thereafter up to $2,250, after which there is no coverage or a "donut hole" until the patient reaches $5,100 in total drug costs, after which they pay only 5% in co-pay. In addition, the patients must pay a monthly premium of $25-40, depending on their specific plan. The plan itself is offered by participating private insurers who in turn are subsidized by Medicare. Patients must sign up for Part D coverage by May 1, 2006 or risk paying higher premium (e.g, which could escalate by 1% per month). For patients on high cost drugs, the co-pay and premium can exceed $4,000 per year, which for lower income families can represent a life-transforming burden (the average US household has about $45,000 of annual income spread across 2.6 family members). Likewise, some patients with Part B coverage also face a 20% co-pay on their treatments.

Historically, the pharmaceutical industry has supported efforts by institutions, such as disproportionate share hospitals (DSH), to assist many of the Medicare uninsured or underinsured with free drugs. Now that the Part D program is operational, there will be fewer uninsured Medicare patients, as many will choose to enroll in the Part D benefit. However, given the design of the Part D program and the associated high co-pays, many of these patients will be underinsured and still unable to afford their medications. Under the "donut hole" coverage structure of the Part D benefit, many patients that currently are on drug-for-free programs face out-of-pocket costs as high as $4,000 per year (e.g. for a biologic drug that costs $15,000/year). Pharmaceutical providers have offered to discount these drugs, but are wary of running afoul of the anti-kickback statutes. To summarize, the relevant statutes include:

1. Civil Monetary Penalties (CMP) provision (Social Security Act §1128A (a)(5)): Civil statute prohibiting the giving of something of value to Medicare or Medicaid patients that the donor knows, or should know, is likely to influence the patient's selection of a particular provider or supplier of any item payable by Medicare or Medicaid.

2. Anti-kickback statute (Social Security Act §1128B(b)): Criminal statute prohibiting the knowing and willful offer, payment, solicitation, or receipt of any remuneration to induce or reward referrals of items or services payable by a Federal health care program. Remuneration includes transfer of anything of value, directly or indirectly, overtly or covertly, in cash or in kind. The "one purpose test" is relevant, i.e. if you do 15 things that are all good but one that violates the anti-kickback statues, then you are liable. Statute applies to parties on both sides of the transaction.

With the latest guidelines provided by the OIG, there are two broad ways (or models) for helping the Medicare covered financially needy without running afoul of the federal anti-kickback statutes. Model 1 is the "outside of the Part D" model under which pharmaceutical providers can distribute free drug to the financially needy, so long as the recipients do not apply any part of the implied value of the drug towards their co-pays or TrOOPs (True Out Of Pocket expense) under the Part D coverage. Further, the donor pharmaceutical provider must inform the Centers for Medicare and Medicaid Services (CMS) appointed Coordinator of Benefits (COB) about the subsidy so that it can inform the Part D plans administrating the coverage. Model 2 is the "inside the Part D" model under which the pharmaceutical provider can provide a cash subsidy to the patient through an independent charity, as described above.

Currently, pharmaceutical drug manufacturers are allowed to assist the uninsured patients through "bulk drug replacement patient assistance programs (PAP)." In these cases, pharmaceutical providers (or their affiliated PAPs) provide in-kind donations in the form of free drugs to pharmacies, health centers, clinics, and other entities that dispense drugs to qualifying uninsured patients directly. These programs potentially implicate the Federal anti-kickback statute if the free drugs are given to a recipient that is in a position to generate Federal healthcare program business for the donor manufacturer. In evaluating such a program the OIG looks at a number of factors and the safeguards in place to: (1) protect the Federal health care program beneficiaries from being steered to particular drugs based on the financial interests of their health care providers or suppliers, (2) protect the Federal health care program from increased costs, and (3) ensure that bulk drugs are not improperly charged to Federal health care programs.

Separately, the OIG has also allowed pharmaceutical providers to provide cash assistance to the underinsured, "inside of Part D" through independent charities or foundations. There are five OIG mandated requirements that apply to such arrangements: (1) the manufacturer can have no influence or control over the program, (2) the assistance is awarded in a truly independent manner (i.e., no link between a manufacturer's donation and beneficiary's receipt of assistance), (3) the assistance is awarded without regard to the manufacturer's interests or beneficiary's choice of provider (i.e. which doctor or pharmacy), (4) the assistance is awarded based on reasonable, verifiable, and uniform measures of financial need, and (5) there is no data exchange that allows a manufacturer to correlate its donations to the number of prescriptions subsidized by the charity. Contributions can be limited to specific disease states, but not so narrowly that only one of many available brands qualifies. Product contributions (in lieu of cash), while eligible for TrOOP (patient's True Out Of Pocket Costs or co-pay) per CMS, are problematic since they can create a direct correlation between the donation and the use of the product, particularly if that one brand is the only option offered by the charity.

There are a number of foundations that assist under-insured patients with out-of-pocket costs. They include Patient Services Inc. (PSI), Patient Advocate Foundation, Chronic Disease Fund, National Organization for Rare Disorders. Patient Access Network Foundation (PANF) and the Healthwell Foundation.

As a means of helping Medicare Part D enrollees meet their cost sharing obligations and operate "inside of Part D", institutional PAPs are problematic. Institutional PAPs create the same heightened risk of violating the anti-kickback statute as traditional PAPs because they create an incentive for a safety net provider to steer Part D enrollees towards the sponsoring pharmaceutical provider's products. In addition, the PAPs can create compliance risks if the pharmaceutical providers are offered an inducement to have their products included in the foundation's formulary. The OIG also warns that institutional PAPs raise "substantial risks related to accounting for the amount of replacement drug that would be equivalent to the cost-sharing amount owed by the beneficiary; properly attribute that amount to beneficiaries; and properly calculating TrOOP."

As a means of helping uninsured patients with free drug, operating "outside of Part D", whereby patients may not apply any value of the free drug towards their TrOOP or cost-sharing obligations, the institutional bulk drug programs also face challenges. This is because the institutional programs cannot award assistance without regard to the providers or suppliers used by the enrollee, since the drugs available are from only manufacturers that voluntarily participate in providing free drugs to the hospital.

The allowed independent charity or foundation model has not been adapted for institutions in any significant manner for use with either inside or outside of Part D models and thus does not help institutions in their efforts to aid the underinsured. Further, while the independent charity model offers many benefits and helps to address a number of concerns around the Civil Monetary Provisions and the Anti-Kickback statutes, over the few years, a number of limitations of this model have become evident.

Drug manufacturers are reluctant to contribute funds given the strong possibility of subsidizing direct non-generic competitors: Drug manufacturers are willing to assist under-insured patients by discounting their drugs substantially in some form or fashion, while still retaining a positive contribution margin. This is different from programs directed at the uninsured, where the manufacturers give away free drug effectively at a loss up to the limits of their charitable budgets and means. Currently, a foundation must assist patients without regard to the brand of drug prescribed, including generics. This ensures that a physician's treatment choice is not biased towards brands that provide assistance, but is instead determined solely based on medical need. Also, in this way generic drugs, which provide an important policy lever for reigning in health costs, are not disadvantaged even when they choose not to participate in such subsidy/discount arrangements.

While many pharmaceutical companies are prepared to let generics compete on equal footing relative to assistance, they are unwilling to fund other direct competitors that offer drugs no different from theirs relative to price or efficacy: In fact, as shown in the following analysis, unless a manufacturer were certain that each player in the industry was doing its share, not only is the cost of assistance high but, worse, the benefits can accrue to their arch enemy or to free riders. In these cases, the system creates an incentive for the manufacturer to try to game the system in some manner to ensure that, in fact, its brand captures the majority of the subsidized prescriptions. In other cases, it dissuades many pharmaceutical companies from stepping up their contributions to support the underinsured.

Most drug manufacturers support one foundation—often one that is different from the one supported by their direct competitor: FIG. 1 shows economics of a drug manufacturer supported foundation assuming their brand has a 30% market share of new patients. This case study uses numbers fairly typical for manufacturers of biologic drugs. The analysis shows that the sponsoring manufacturer suffers a net contribution loss of $1,906 per patient. But worse still, the donor contributes $8,400 (i.e., $12,000-$3,600) in revenues per acquired patient to the competitors. Some of this would be obviously compensated back in the form subsidies from the competitor's foundation. However, to be certain of that, a drug manufacturer would have to assume that the competitor favored foundation was not gaming the system in some manner. As we know from the theory of economics, in any highly competitive industry, such indirect collusion is highly unlikely.

It was OIG's intent to create a system that does not disadvantage generic and low cost therapies, but not one where smaller share competitors are disadvantaged or that any drug manufacturer is in the uncomfortable position of helping competitors that deliver no cost benefit to the Medicare system. FIG. 2 shows that larger share competitors have greater certainty of positive contribution, for a typical manufacturer with the economic structure shown in Exhibit 1. Conversely, new market entrants, that by definition have low share, face the highest penalties in participating in foundation based programs to assist the underinsured. Once new patient market share (or in other words the share of manufacturer funding that goes towards their own brand), exceeds 50%, the foundation model becomes unconditionally viable. In even markets with modest competition, 50% or greater shares are unlikely.

The separation between the foundation and the drug manufacturer is not robust since the economic interests of the foundations and the donor are nearly completely aligned: The primary source of funding for most of the current foundations is a single pharmaceutical company per disease state. However, as discussed above, the pharmaceutical companies would be unwilling to contribute without some level of assurance that the majority, though not necessarily all of their funding, is going towards their own drugs. Hence, there is a built-in economic incentive for a foundation to "whisper in" some assurances to the manufacturer about their share of the funding in order to curry the favor of the donor and obtain increased funding.

In fact, some of the leading foundations (and their initial board member appointments) have been set up by reimbursement companies that do significant business with both the foundations they have set up and the pharmaceutical companies. Further, there is no oversight mechanism over the foundations to ensure that no gaming goes on. Since eligibility criteria are set and interpreted by the foundations individually, without external audits, there can also be sufficient latitude to game the system in a variety of ways.

Poor patient experience, inefficiency and hence added cost in the system: Currently, it makes sense for a patient to apply to as many foundations as possible (in some cases as many as three to seven) since she cannot be sure which ones actually have funds, will approve her application, and for what amount. Each foundation has its own application process and eligibility requirements. For elderly patients, already burdened by the complexity of Part D plan choices, this is yet another daunting challenge.

The lack of uniform eligibility criteria runs counter to the OIGs desire for increased consistency and objectivity in the approval of all applications. Finally, since multiple foundations are processing applications independently for each patient, there are needless costs to the system as a whole, which ultimately detracts funds available for patients.

Further, since the foundations compete with each other for patients, there is an incentive for each foundation to make a more generous offer than the other, provided they have funding. As each foundation has its own eligibility criteria and latitude in assistance determination, and there is no standardization or audits, it is hard to tell how rampant this problem is. This can inadvertently remove the co-pay pressure on the patient and make them indifferent to even high treatment costs.

No incentive for generic manufacturers to contribute: Given their price points, generic manufacturers have no incentive to contribute to the foundations. For every branded manufacturer they end up subsidizing, the needed sales of their own generic drug will be impossibly high.

SUMMARY OF INVENTION

The present inventive concepts relate to a method of providing a pharmaceutical clearinghouse configured for providing pharmaceutical subsidies to independent Financial Need Assessment Agents (FNA Agents) serving patients under institutional patient assistance programs or PAPs. The clearinghouse of the present disclosure can be implemented outside or inside of Medicare Part D, as examples.

In accordance with one aspect of the invention, provided is a method of providing a pharmaceutical clearinghouse for institutional patient assistance programs (PAPs). The method comprises. establishing a network of FNA Agents, each in-network FNA Agent configured to receive patient requests for drugs under one or more of the PAPs and establishing a network of pharmaceutical providers, each in-network pharmaceutical provider configured to distribute subsidies to satisfy the patient requests. The method also includes establishing a clearinghouse between the network of FNA Agents and the network of pharmaceutical providers, including the clearinghouse receiving a patient request from an in-network FNA Agent, determining a subsidy required to satisfy the patient request from one or more of the in-network pharmaceutical providers, directing the subsidy from the one or more in-network pharmaceutical providers to the in-network FNA Agent in response to the request. And the method includes maintaining independence between the in-network FNA Agents and the in-network pharmaceutical providers.

The subsidy can only be in-kind drug available from one or more of the in-network pharmaceutical providers.

The clearinghouse can determine if the drug is available from an in-network pharmaceutical provider.

If the drug is available from the in-network pharmaceutical provider the method can include the in-network pharmaceutical provider providing the subsidy in the form of only in-kind drug.

If the drug is available from the in-network pharmaceutical provider the method can include the in-network pharmaceutical provider providing the subsidy in the form of in-kind drug and cash.

If the drug is available from the in-network pharmaceutical provider the method can include establishing a fair market value of the drug by the in-network pharmaceutical provider providing at least a portion of the subsidy in the form of cash and procuring the drug on the open market with the cash.

If the drug is not available from any in-network pharmaceutical provider, the method can include the clearinghouse determining an amount needed to procure the drug and the clearinghouse determining a cash portion of the amount to be paid by one or more of the in-network pharmaceutical providers.

Determining the cash portion can include determining a pro rata portion to be paid by each of the in-network pharmaceutical providers, including determining the pro rata portion as a function of the total amount of all subsidies provided by the in-network pharmaceutical providers.

The method can include the patient submitting a single application and a plurality of FNA Agents processing the application to generate competitive offers to obtain the subsidy and provide the drug.

The method can further comprise the clearinghouse establishing a low-cost pharmaceutical provider threshold, whereby in-network pharmaceutical providers that provide drugs that cost less than the low-cost threshold do not subsidize in-network pharmaceutical providers having drugs that cost more than the low cost threshold.

The method can further comprise the clearinghouse establishing a low-cost pharmaceutical provider threshold, whereby in-network pharmaceutical providers that provide drugs that cost less than the low-cost threshold provide subsidies in a smaller proportion than the in-network pharmaceutical providers having drugs that cost more than the low cost threshold.

The method can further comprise establishing a uniform and auditable standard of patient need assessment to determine eligibility for the subsidy.

The method can further comprise providing the subsidy in the form of one or more coupons that can be applied against the drug costs and patient co-pay for any drug in a given disease state.

The method can further comprise generating an order for obtaining the subsidy from a designated third party wholesaler.

The method can further comprise generating an order for obtaining the subsidy from an institutional represented by the FNA Agent.

In accordance with another aspect of the invention, provided is a pharmaceutical clearinghouse system for institutional patient assistance programs (PAPs). The clearinghouse system comprises: a set of FNA Agent modules configured to establish a network of FNA Agents, each in-network FNA Agent configured to receive a patient request for a drug under one or more of the PAPs; a set of pharmaceutical provider modules configured to establish a network of pharmaceutical providers, each in-network pharmaceutical provider configured to distribute subsidies to satisfy the patient requests; and a set of subsidy module configured to determine a subsidy required from one or more of the in-network pharmaceutical providers to satisfy a patient request for a drug received from an in-network FNA Agent, and to direct the subsidy to the FNA Agent. The clearinghouse system is configured to maintain independence between the in-network FNA Agents and the in-network pharmaceutical providers.

The subsidy can be only in-kind drug available from one or more of the in-network pharmaceutical providers.

The set of subsidy modules can be configured to determine if the drug is available from an in-network pharmaceutical provider.

If the drug is available from the in-network pharmaceutical provider, the set of subsidy modules can be configured to request the subsidy from the in-network pharmaceutical provider in the form of only in-kind drug.

If the drug is available from the in-network pharmaceutical provider, the set of subsidy modules can be configured to request the subsidy from the in-network pharmaceutical provider in the form of in-kind drug and cash.

If the drug is available from the in-network pharmaceutical provider, the set of subsidy modules can be configured to establish a fair market value of the drug by requesting the in-network pharmaceutical provider to provide at least a portion of the subsidy in the form of cash to enable procurement of the drug on the open market with the cash.

If the drug is not available from at least one in-network pharmaceutical provider, the set of subsidy modules can be configured to determine an amount needed to procure the drug; and determine a cash portion of the amount to be paid by one or more of the in-network pharmaceutical providers.

The set of subsidy modules can be configured to determine a pro rata portion of the cash portion to be paid by each of the one or more in-network pharmaceutical providers, as a function of the total amount of all subsidies provided by the in-network pharmaceutical providers.

The clearinghouse system can be configured to make the patient request accessible by a plurality of the in-network FNA Agents to enable the plurality of in-network FNA Agents to generate competitive offers to obtain the subsidy and provide the drug.

The clearinghouse system can be configured to establish a low-cost pharmaceutical provider threshold, and the set of subsidy modules is configured to determine the subsidy such that in-network pharmaceutical providers that provide drugs that cost less than the low-cost threshold do not subsidize in-network pharmaceutical providers having drugs that cost more than the low cost threshold.

The clearinghouse system can be configured to establish a low-cost pharmaceutical provider threshold, and the set of subsidy modules is configured to determine the subsidy such that in-network pharmaceutical providers that provide drugs that cost less than the low-cost threshold provide subsidies in a smaller proportion than in-network pharmaceutical providers having drugs that cost more than the low cost threshold.

The clearinghouse system can be configured to establish a uniform and auditable standard of patient need assessment to determine eligibility for the subsidy.

The clearinghouse can be configured to generate the subsidy in the form of one or more coupons that can be applied against the drug costs and patient co-pay for any drug in a given disease state.

The set of subsidy modules can be configured to generate an order for obtaining the subsidy from a designated third party wholesaler.

The set of subsidy modules can be configured to generate an order for obtaining the subsidy from an institutional represented by the FNA Agent.

BRIEF DESCRIPTION OF THE DRAWINGS

The drawing figures depict preferred embodiments by way of example, not by way of limitations. In the figures, like reference numerals refer to the same or similar elements.

FIG. 1 is a table showing a prior art example of typical pharmaceutical provider economics.

FIG. 2 is a table showing an example of market share information that could be used by the clearinghouse for determining pro rata shares of contributions by registered pharmaceutical providers for pharmaceuticals offered by unregistered pharmaceutical providers.

FIG. 4 is a table showing a clearinghouse example where registered pharmaceutical providers contribute toward drugs offered by out-of-network providers.

FIG. 5 is a table showing a clearinghouse example involving a low-cost pharmaceutical provider.

DETAILED DESCRIPTION OF PREFERRED EMBODIMENT

A pharmaceutical clearinghouse establishes relationships with a set of Financial Need Assessment Agents (FNA Agents) representing a set of institutions, and a set of pharmaceutical providers. An FNA Agent, as used herein, can be a foundation, qualified independent entity, or the disbursement office within an institution having a patient assistance program (PAP), or any other entity recognized by the OIG as able to serve such role, in the present context. An institution can be a hospital or other healthcare entity, or any other entity recognized by the OIG as able to serve such role, in the present context. A pharmaceutical provider, as used herein, can be a drug company or manufacturer or other entity recognized by the OIG as able to serve such role, in the present context. Optionally, a set of Designated $3^{rd}$ Party Wholesalers (D3PWs) of pharmaceuticals could be provided to assist in distributing pharmaceuticals.

Figure 3A:
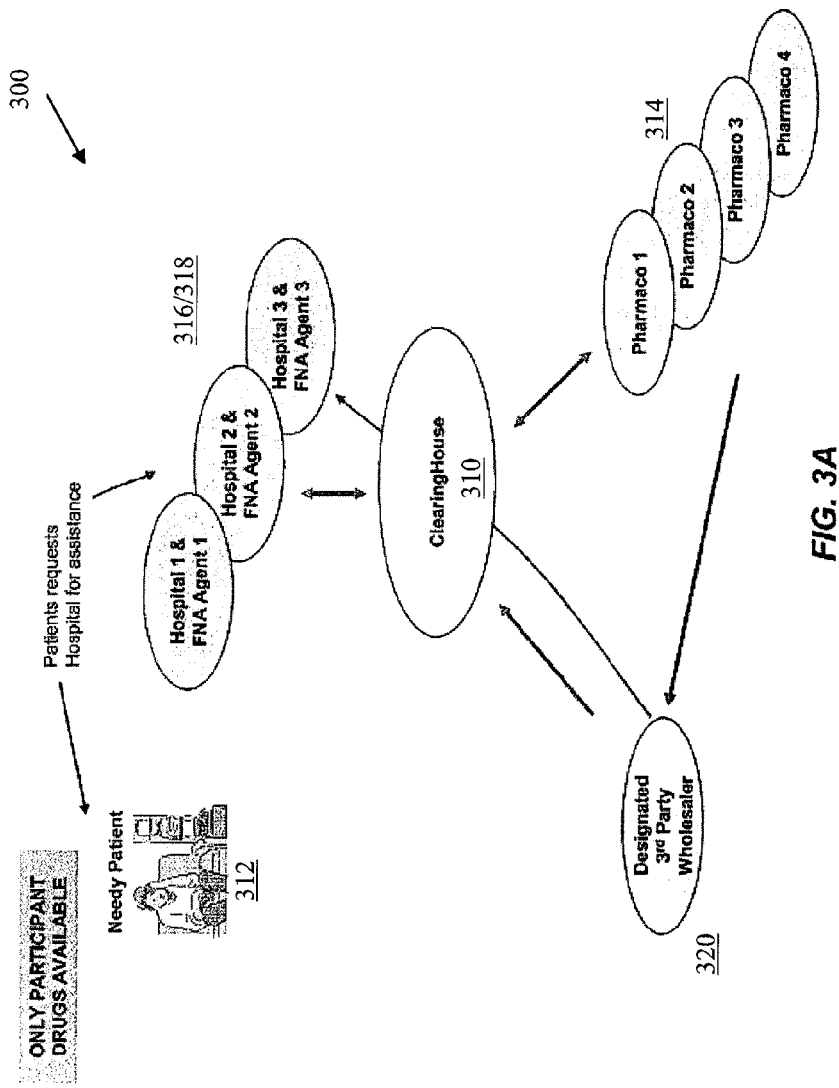
FIG. 3A is a block diagram of an embodiment of an institutional clearinghouse model "outside of Part D" and FIG. 3B is a block diagram of an embodiment of an institutional clearinghouse model "inside of Part D."
Figure 3B:
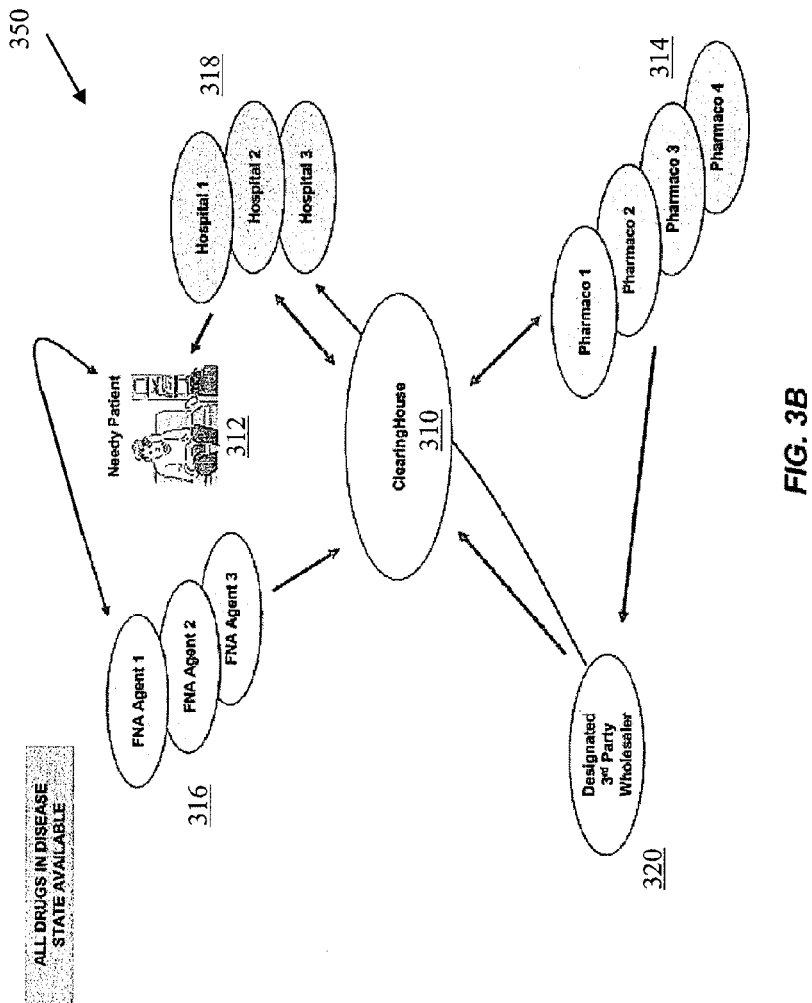

In response to the clearinghouse receiving a patient request for a pharmaceutical from an FNA Agent representing an institution with a PAP, the clearinghouse obtains or otherwise directs a subsidy from at least one pharmaceutical provider and provides the subsidy to the FNA Agent (e.g., see Model 2 of FIG. 3B). In some embodiments, the institution itself can act as (or include) the FNA Agent by establishing an independent office that disburses subsidies to patients without regard to their use of the institution's services (e.g., see Model 1 of FIG. 3A). Systems, methods, and computer program products can implement the clearinghouse in a variety of forms, without departing from the present invention. The subsidy may be in the form of cash, in-kind pharmaceutical (e.g., drug), or a combination thereof. What follows are embodiments of various aspects of the present invention.

The current model for assisting the under-insured relies on a single "black-box", namely a foundation, to separate the patient from the donor pharmaceutical provider. To address the problems with this model, one needs to have two "black boxes" in tandem between the patient and the pharmaceutical provider, to make the system of giving and receiving assistance "double-blind." Additionally, to address efficiency and effectiveness concerns, the second "black-box" should also function as a clearinghouse, much as MasterCard/Visa serve the credit card industry and Galileo/Sabre serve the travel industry.

In various embodiments of the pharmaceutical clearinghouse for institutions, participating pharmaceutical providers funnel their subsidies for at least one disease state (e.g., rheumatoid arthritis, diabetes, Alzheimer's, and so on) through at least one clearinghouse, which in turn allocates and passes along the subsidies to enrolled (or "in-network") FNA Agents. The FNA Agents continue to deal with patients as they currently do, but no longer receive direct funding directly from the pharmaceutical providers, e.g., drug manufacturers. Each FNA Agent sends its applications to the clearinghouse and receives subsidies to address patients requests, e.g., full or partial funding, the pharmaceutical, or a combination thereof.

For illustrative purposes, provided herein are two examples of models within which the institutional clearinghouse of the present disclosure can be implemented: Outside Part D and Inside Part D.

FIG. 3A shows an embodiment of a clearinghouse 310 used in an Outside Part D model, e.g., Model 1 300. Each participating pharmaceutical provider (e.g., Pharmacos 1-4 314) funds all patients (e.g., patient 312) that are prescribed the pharmaceutical provider's brand, e.g., up to the limits set by the pharmaceutical providers. Typically, the limit is a single limit across all enrolled institutions 318, e.g., Hospitals 1-3; it is not allocated to individual institutions, therefore participating pharmaceutical providers are not able to favor any one FNA Agent over another, e.g., FNA Agents 1-3 316. The institutions provide subsidies, e.g., free drug of only the donor pharmaceutical providers 314. The patient 312, which is usually uninsured or indigent, cannot apply any part of the subsidy toward his co-pays or TrOOPs (True Out Of Pocket expense). Unlike prior approaches, the subsidy is provided from the pharmaceutical providers 314 to clearinghouse 310, which directs the subsidy to the appropriate FNA Agent and institution, e.g., FNA Agent 1 and Hospital 1 316/318. In various embodiments, a designated $3^{rd}$ part wholesaler 320 can provide the subsidy, e.g., free drug, to clearinghouse 310 on behalf of pharmaceutical providers 314.

FIG. 3B shows an embodiment of a clearinghouse 310 used in an Inside Part D model, e.g., Model 2 350. Each participating pharmaceutical provider (e.g., Pharmacos 1-4 314) not only funds all patients that are prescribed the pharmaceutical provider's brand, but also contributes an allocated share of cash funds to cover all of the other patients requesting drugs provided by non-participating pharmaceutical providers, e.g., drug manufacturers (not shown). In one embodiment, the clearinghouse 310 is implemented such that the participating pharmaceutical providers 314 know exactly how much of their funding was used on their own drugs. Thus, the participating pharmaceutical providers 314 would neither be able to favor any one FNA Agent over the other, nor have anything material to gain from doing so. Also, the information would be likely the same as, or at least consistent with, that computable from publicly available market share information of known participating pharmaceutical providers. In this embodiment, pharmaceutical providers 314 may set no limits on their participation since they will likely have a positive profit contribution even after the subsidy.

In the Inside Part D Model of FIG. 3B, pharmaceutical providers 314 can provide subsidies in a mix of cash and free drug (e.g. 80% free drug and 20% cash). To avoid possibilities of patient steering toward the brands of the donor pharmaceutical providers 314, the clearinghouse 310 can use the cash provided by pharmaceutical providers 314 to cover the brands of non-participating drug manufacturers to purchase those drugs on the open market, e.g., at wholesale from the D3PWs 320, in the same proportions (e.g. 80% free drug and 20% cash) and disburse them accordingly through the FNA Agents 316.

In the preferred form of either model, i.e., Outside Part D or Inside Part D, each patient needs only to apply to one FNA Agent of their choice. This eliminates duplicate processing caused when patients apply to multiple FNA Agents. The clearinghouse 310 treats each of the FNA Agents 316 substantially the same—it preferably does not favor one FNA Agent over another.

Role of the Financial Need Assessment Agent (FNA Agent): An FNA Agent 316 can be any entity previously described, and should be independent of influence from the donor pharmaceutical providers 314. The FNA Agent may also optionally be independent of the institution (e.g., Hospital, as in Model 2 of FIG. 3B). As mentioned above, the FNA Agent can be a foundation, qualified independent entity, or the disbursement office within an institution. The FNA Agent is responsible for processing the applications of patients referred by an institution under a PAP, and authorizing the disbursement of subsidies. In the Outside Part D model, the subsidies will likely be all in-kind pharmaceuticals and, upon authorization, can be disbursed by the institution out of its bulk replacement drug inventory, for example. The pharmaceutical could also be provided directly from a pharmaceutical provider 314 or D3PW 320.

In the case of an Inside Part D model, as in FIG. 3B where subsidies may be in cash, in-kind, or a combination thereof, the institution 318 (e.g., hospital) can disburse in-kind drug out of its bulk replacement drug inventory and cash subsidies through the FNA Agent. That is, in the preferred form, the FNA Agent should not favor one pharmaceutical provider over another. Patients may work with any FNA Agent of their choice based on their perception of its quality of service. Preferably, the amount of funding approved for the patient from one FNA Agent to the next will be substantially the same—because each patient request is preferably honored by the clearinghouse 310, regardless of the FNA Agent that submitted it. While an FNA Agent can canvas pharmaceutical providers to contribute subsidies for current and future disease states, which it should as an advocate of patient care, all subsidies would flow through (or under the direction of) the clearinghouse 310 to all enrolled FNA Agents 316 (and not just the canvassing FNA Agent) and institutions 318. In the preferred form, the FNA Agents would not receive any funds directly from a participating provider for a given disease state, unless under the direction of the clearinghouse 310.

Role of the Clearinghouse: The clearinghouse is responsible for informing participating pharmaceutical providers (e.g., drug manufacturers) of their allocated share of the needed subsidies, and then collecting and disbursing (or otherwise directing) the subsidies appropriately to each FNA Agent and institution. In the preferred embodiment, subsidies are not provided to any patients directly, but in various other embodiments it may be allowed with appropriate assurances and accountability. Additionally, the clearinghouse could host a number of shared processes to increase efficiencies (e.g., lower cost, improve response time, etc.) and enforce standardization. The clearinghouse can also audit the FNA Agents, institutions, and the D3PW to ensure process conformance. The clearinghouse can also reconcile inventory and disbursements across the FNA Agents, institutions, D3PWs and the pharmaceutical providers.

In various embodiments, the clearinghouse can do one or more of: (1) track and reconcile patient assistance to dispensed inventory; (2) place bulk orders for all hospitals with the pharmaceutical providers; (3) track and reconcile shipments to hospitals; (4) bill hospitals and D3PW for any missing inventory, e.g., at average sale price (ASP) and reimburse the appropriate pharmaceutical providers; and (5) inform the COP of TrOOP usage for each patient.

Role of the Designated $3^{rd}$ Party Wholesaler/s (D3PW): The D3PW is an entity that can be optionally included to assist in the distribution or disbursement of pharmaceutical subsidies. When included, the D3PW is responsible for processing orders for drugs from institutions and shipping them. The D3PW receives the drugs in bulk from the pharmaceutical providers. The D3PW can disperse drug in response to an order from the clearinghouse, which can be generated as a result of a patient request submitted by an FNA Agent. But the D3PW need not know the quantities ultimately shipped to each institution. The D3PW is fully responsible for reconciling its inventories and disbursements with the clearinghouse.

Role of the institutions: The institutions evaluate the insurance coverage of patients and refer patients requiring assistance to the FNA Agents. For example, if the institutions have PAPs, the FNA Agents can act on behalf of the institutions and their respective PAPs. Once the patient request is processed through an FNA Agent and the clearinghouse, the institution can dispense the drug under the direction of the clearinghouse, e.g., from the institution's bulk supply. The institutions can place periodic replacement orders for the dispensed drugs with the D3PWs. The institutions will be fully responsible for reconciling their inventories and disbursements with clearinghouse.

How the process works—Preferred Embodiment: Typically, a patient goes to a particular institution with a health issue. In the course of his treatment, the patient is prescribed a particular drug. If the patient does not have the means to fully pay for the drug, e.g., because he is uninsured and indigent or because his insurance coverage is inadequate, the patient can request assistance under a PAP of the institution. The institution, in turn, can refer the patient to an FNA Agent, which in some cases can operate out of the institution's business office.

In the illustrative embodiment, the clearinghouse furnishes the FNA Agent with a standardized application for the disease state covering the requested brand. Given a standardized application criteria and methodology, the amount of financial assistance from one FNA Agent to the next, and hence also from one institution to the next, will not vary significantly. Upon completion of the application, the FNA Agent will inform the clearinghouse of the amount of assistance requested and the clearinghouse will authorize its disbursement to the institution. In general, the clearinghouse will not collect or review the applications and the only information it will have, in this embodiment, is the patient's social security number, brand of drug prescribed, the name of the requesting institution, and the amount of financial assistance required for such patient requested pharmaceutical. In other embodiments, it may be allowable for the FNA Agent itself to authorize the disbursement of the subsidy to the institution in order to minimize handoffs and increase process efficiency. Once the institution receives the authorization, it can disburse any free drug subsidy from its bulk inventory. If the subsidy is in cash, the cash can be disbursed by the FNA Agent directly to purchase the required drug.

In the Outside Part D model, e.g., as in the embodiment of FIG. 3A, at the end of each month, the clearinghouse can compute the total subsidy disbursed across all brands by all participating institutions for a given disease state and can place bulk orders with donor pharmaceutical providers to deliver the drugs to D3PWs.

In the Inside Part D model, e.g., as in the embodiment of FIG. 3B, at the end of each month, the clearinghouse can compute the ratio of the total funds disbursed across all brands to and by all participating foundations for a given disease state versus the total funds needed to cover the brands of the in-network pharmaceutical providers. For example, if the disease state is rheumatoid arthritis and the clearinghouse and FNA Agents disbursed $138K for bands offered by participating+non-participating pharmaceutical providers, with $100K for brands offered by participating pharmaceutical providers for the disease state, then the ratio is $138K/$100K, which is 138%. Next, each pharmaceutical provider would be asked to fund fully the amount needed to cover its brand plus the percentage needed to cover non-participating (or out-of-network) pharmaceutical providers brands (i.e. the 38% or $38K).

FIG. 3B illustrates how the clearinghouse works in this embodiment. The extra $38,000 can be divided among the participating pharmaceutical providers in any of a variety of manners. But in the preferred embodiment, each provider pays a pro rata share of the $38,000. So, if Pfizer, Inc. was a participating provider and disbursed $25,000 for its own drug (i.e., out of the $100,000), then Pfizer, Inc. would pay 25% of the $38,000, and so on. The $38,000 could be used to purchase drugs of non-participating pharmaceutical providers on the open market, e.g., from wholesalers such as D3PW 320 in FIGS. 3A and 3B.

Other Aspects of the Illustrative Preferred Embodiment

In various embodiments, the clearinghouse can set uniform criteria for enrolling FNA Agents, in what can be considered a network of FNA Agents and institutions. Pharmaceutical providers (e.g., drug manufacturers) will have no involvement in the enrollment process. Generally, all FNA Agents that offer competitive costs and quality of service will be allowed to join the network. Examples of situations in which an FNA Agent may not be allowed to join in the network may include one or more of the following: the FNA Agent's administrative charges are significantly higher than the norm relative to others in the network; the FNA Agent has been set up to assist just small amount (e.g., 1-2) patients when the norm for others is much greater (e.g., 500+); the FNA Agent has been found to violate the required processes for evaluating patient need and eligibility; the FNA Agent has been found to or is reasonably believed to have engaged in unethical or illegal conduct, etc. However, as a general matter, the clearinghouse 310 will, in most instances, be inclined to enroll more, not fewer FNA Agents. Likewise, any institution that meets a uniform criteria defined by the clearinghouse will typically be allowed to join the network and access subsidies from any and all enrolled pharmaceutical providers in the network.

In various embodiments, the clearinghouse 310 preferably has no role in evaluating patient applications or determining the amount of assistance. The clearinghouse merely matches subsidies (e.g., cash, in-kind drug, or both) efficiently to the FNA Agents that request the assistance. The FNA Agents will bear the responsibility, as they often currently do, for attracting, evaluating, processing, and approving patient applications per standardized criteria. The FNA Agents can then disburse their subsidies received via the clearinghouse 310.

In various embodiments, eligibility criteria for privately insured patients will be designed to be the same or similar to those used for Medicare patients, except where disallowed by existing contracts with such insurers. Specifically, they will generally not be more generous towards Medicare patients. This ensures that the cost control pressures that private insurers apply towards their own patients (e.g. up-tiering generics, requiring prior-authorizations, or failure of lower costs therapies first, etc.) are equally felt by Medicare patients subsidized by the United States Federal government.

In various embodiments, the eligibility criteria will consider income and assets for patients requiring acute therapy and income and available annual cash-flow for chronic therapies. Hence, such criteria may cover income, local cost of living, family size, expenses, scope and extent of patient medical bills, co-pay gap versus current payments, etc. The criteria may be somewhat different by disease state, i.e. more generous for high cost therapies. To ensure that patients are only receiving funding to the level they need and not needlessly eliminating cost pressures, the application will be reasonably thorough.

In various embodiments, the clearinghouse 310 and the pharmaceutical provider will have no direct contact with the patients in the processing their application.

In various embodiments, the FNA Agents and patients will receive no direct funds for the disease state from the pharmaceutical provider (e.g., drug manufacturer).

In various embodiments, the FNA Agents will disburse assistance purely on the basis of patient financial need, without regard to the brand prescribed.

In various embodiments, participation in the clearinghouse models 300 and 350 by pharmaceutical providers and the FNA Agents is entirely voluntary. Preferably, for any given disease state, the pharmaceutical provider (e.g., drug manufacturer) can provide assistance directly to an in-network FNA Agent or through the clearinghouse 310, but not both simultaneously in a given balance of calendar year.

In various embodiments, assistance to existing patients in all of the in-network FNA Agents (typically foundations) will also flow through the clearinghouse 310 in the future to simplify transaction processing and lower system costs. Patients themselves will see no difference in their interactions since they will continue to deal with the FNA Agent with which they currently work. However, they will be required to give permission to the FNA Agent to transfer the required information to the clearinghouse 310 as a condition for future continuation of funding. Most FNA Agents already require patients to re-qualify annually and this would be added to all future re-qualification requests.

In various embodiments of the Inside of Part D model 350, the clearinghouse 310 can require all in-network pharmaceutical providers (i.e., those registered with the clearinghouse) to provide sufficient funding to cover all patients—i.e. the clearinghouse will always fully clear. There can be unforeseen situations in which for one reason or another, a pharmaceutical provider is unable to meet its full financial commitment. In those situations, its brand's share of the patients could be proportionally reduced, the clearinghouse will not fully clear and there will be a waiting list.

In various embodiments of the Outside of Part D model 300, the clearinghouse can require all in-network pharmaceutical providers (i.e., those registered with the clearinghouse) to provide funding up to a limit of their own choosing. Subsidies for the pharmaceutical providers' respective brands can be disbursed up to the limit, after which point patient requests can be either turned down or held in a waiting list.

Some of the issues with the current institutional models that can be addressed by the illustrative embodiment of a clearinghouse include:

More robust compliance with the OIG intent: In various embodiments, the pharmaceutical providers have no direct transactional relationship with the in-network FNA Agents or institutions, unless directed or managed by or through the clearinghouse. Further, the pharmaceutical provider should be indifferent as to which FNA Agent or institution actually disburses the subsidies to the patients, so long as the FNA Agent's administrative charges are competitive. The FNA Agent, in turn, should be indifferent as to the source from which clearinghouse secures its subsidies, since all approved patients are provided the requested assistance to the point such subsidy is available. The pharmaceutical providers and institutions have no way to link contract negotiations on which pharmaceuticals are to be on an institution's formulary with the award of subsidies to patients.

Further, given the preferred standardization of application processing, the clearinghouse models 300 and 350 better comply with OIG's desire for a reasonable, verifiable, and uniform process for assessing patient financial need.

Economic context that supports increasing funding from providers: In various embodiments, the clearinghouse models 300 and 350 eliminate the ability of pharmaceutical providers (e.g., drug manufacturers) to game individual FNA Agents and ensure that all in-network pharmaceutical providers share the burden of non-participating pharmaceutical providers evenly. Hence, the participating pharmaceutical providers are assured that they are in effect providing their drugs to the underinsured patients at a discount and not a loss.

FIG. 4 provides a table showing an example of financial implications for a set of FNA Agents A-D using the clearinghouse 310 of FIG. 3B, as an example. In FIG. 4, we see that these discounts can be generous and, in the illustrative case, at 41% (i.e., for providers of Brand X and Brand Z). Also we note that the share of funding of contributing pharmaceutical providers (i.e., for Brand X and Brand Z) applied towards their own brands is 73%, which as we see from FIG. 4 is sufficient to ensure there is a modest, but positive variable contribution from the pharmaceutical providers.

Better patient experience: In various embodiments, the FNA Agents, in effect, will compete for the patients primarily by reaching them first, creating awareness of their programs, and providing excellent service and hand-holding. Further, the patients will need to apply to only one FNA Agent and deal with a single eligibility criteria. Since the system creates a context that encourages pharmaceutical providers to increase funding, fewer patients will need to wait in queues and delay their therapies.

Resource efficiency: In various embodiments, the clearinghouse 310 will help to reduce waste by eliminating the need for multiple FNA Agents to process the same patient applications. Assuming the average patient applies to three (3) FNA Agents, this will cut down the system-wide application processing workload by two-thirds.

Variations to the Clearinghouse Model

Audit of patient applications: In various embodiments, to ensure that the FNA Agents are applying a uniform and fair standard to every patient application, the clearinghouse 310 could audit patient applications, for example, following statistical random sampling methodology. FNA Agents with a poor record of compliance can be sanctioned in a number of ways, including, as possible examples, such control methods as requiring staff to undergo re-training, imposing fines, and/or ultimately removal from the network.

Inform Centers for Medicare and Medicaid Services (CMS) COB (i.e., Coordination of Benefits) of financial assistance: In various embodiments, the clearinghouse 310 can transmit to the pharmaceutical providers information indicating the subsidy approved for the participating FNA Agent patients. For example, the clearinghouse could transmit a single file daily of all cash assistance approved for the participating FNA Agent patients. This will make communication of the benefits to plans easier for CMS.

Allow pharmaceutical providers to contribute in cash or in-kind: In various embodiments, the pharmaceutical providers can provide patients who have been prescribed their drug with free drug up to the value of the approved assistance level. The in-network pharmaceutical provider can still be required to provide cash assistance to patients prescribed brands of other, non-participating pharmaceutical providers. In the example of FIG. 4, Brand Z can supply its 400 patients with, in effect, $1.6M in free drug. However, it must still pay the balance $600,000 in cash to meet its clearinghouse commitment of $2.2M and support low cost Brand Y, which does not participate in the network. Since the FNA Agents can award assistance to patients without regard to the brand prescribed, and all FNA Agents can provide the free drug, this does not create any kind of tie-in. It does improve the ability of pharmaceutical provider to use its funds more efficiently, since free drug distribution usually avoids royalty payments which for many drugs can be equal to the costs of goods sold.

The product distribution to the patients could be contracted by the clearinghouse with potentially third-party vendors (D3PWs) that could take shipment orders directly from any of the network FNA Agents or institutions, under the control, direction or supervision of the clearinghouse per such agreement. In the case of free pharmaceuticals (e.g., drugs), the D3PWs could distribute the pharmaceuticals from their own inventory. Further, in other embodiments, even pharmaceuticals of non-participating pharmaceutical providers could be provided as free pharmaceuticals from inventories of the institutions and/or D3PWs and funded by the excess funds contributed by participating pharmaceutical providers. These non-participating pharmaceutical providers drugs could be purchased from the D3PWs.

Allow low-cost/generic drug manufacturers to not subsidize high-cost/branded drugs: In various embodiments, to encourage low cost and generic drug manufacturers to participate in programs for the under-insured, the clearinghouse 310 can require that a given pharmaceutical provider needs to only subsidize its own drug and any that are no more than 20% more expensive, for example. Hence, generic drug manufacturers that sell their brands at substantial discounts do not need to contribute funds towards higher priced brands even when the physician prescribes those to the patient. This will remove a key barrier from their willingness to contribute to the system. This is illustrated in the revised scenario in FIG. 5, where the low cost Brand Y only pays its own share of the funding (plus that of other non-participating lower cost drugs if there were any), and the burden of supporting premium priced Brand Z falls entirely on Brand X.

Figure 6:
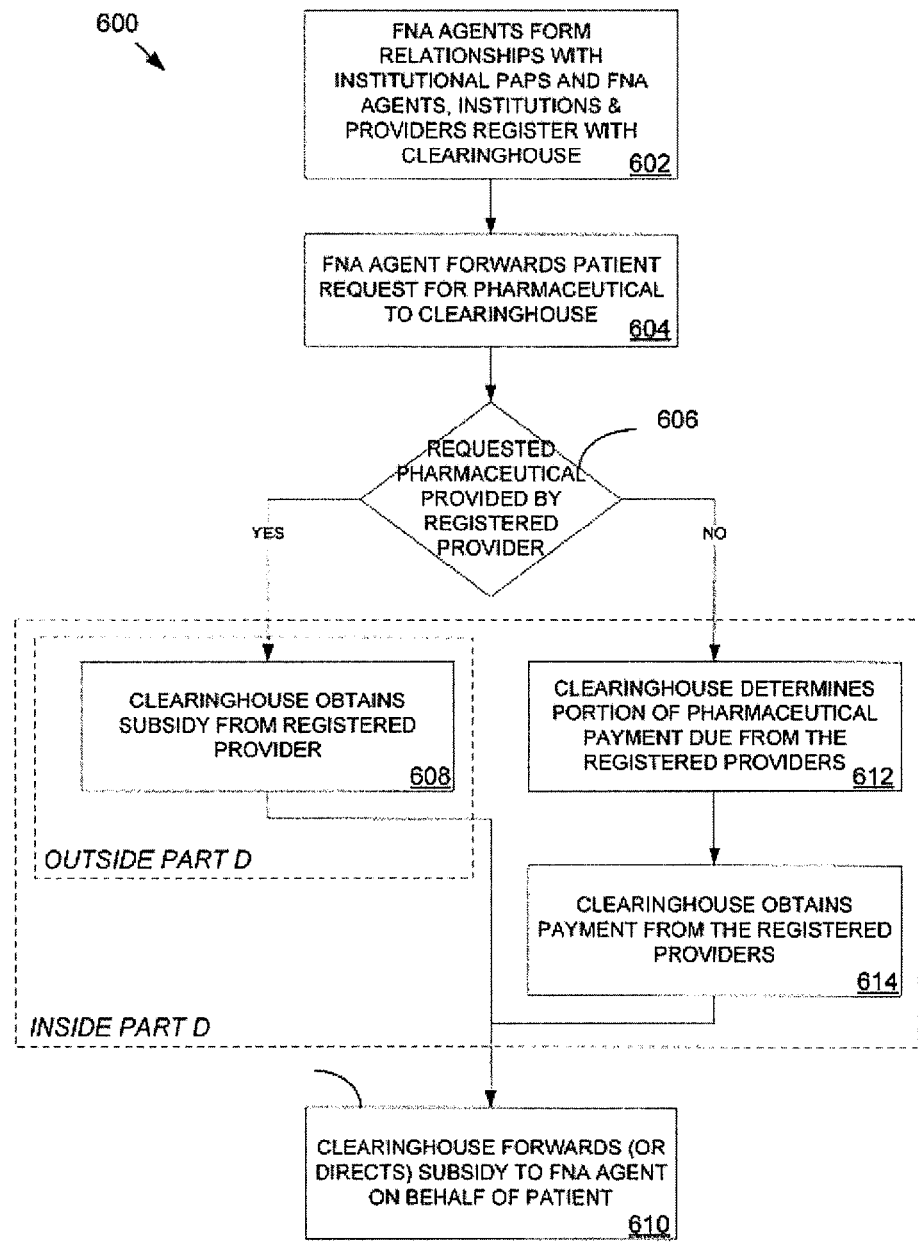
FIG. 6 is a flowchart showing a method of providing an institutional clearinghouse.

FIG. 6 shows a top level flowchart of a method 600 of providing a clearinghouse 310, which can be implemented Outside Part D and/or Inside Part D, as indicated by the correspondingly labeled dashed-line boxes. If not specifically identified as being Inside Part D or Outside Part D, then the step in FIG. 6 could be implemented in either.

In step 602 FNA Agents form relationships with institutional PAPs. The FNA Agents 316, institutions 318, and pharmaceutical providers 314 register with the clearinghouse 310, which could be considered to form a network of FNA Agents, a network of pharmaceutical providers, or a network comprising the FNA Agents, the clearinghouse, and the pharmaceutical providers. In step 604, an FNA Agent that has received a patient's request for a drug (or subsidy), which may have been forwarded by the institutional PAP that the FNA Agent represents. The FNA Agent forwards the patient request to the clearinghouse. In step 606 the clearinghouse determines whether or not a registered pharmaceutical provider provides the requested drug. If a registered pharmaceutical provider does provide the drug, then the process continues to step 608, where the clearinghouse obtains in-kind drug from the pharmaceutical provider, or could obtain cash to buy the drug, or could obtain a combination of the foregoing—all as forms of a subsidy.

If the drug is not provided by an in-network pharmaceutical provider, then the process continues to step 612 where the clearinghouse 310 determines the necessary payments to be obtained from the in-network pharmaceutical providers to purchase the drug from the appropriate out-of-network pharmaceutical provider, or otherwise on the open market. In some embodiments, if an in-network pharmaceutical provider is a low-cost provider (e.g., a generic drug company) of a similar drug for the same disease state and if the cost of the requested drug is above a threshold amount relative to the cost of the low-cost pharmaceutical provider's drug (e.g., 20% more expensive) then the low-cost provider need not be required to contribute anything, or possibly a reduced amount, to the cost of the requested high-cost drug. Regardless, the clearinghouse obtains the payments from in-network pharmaceutical providers in step 614. In step 610, the clearinghouse 310 provides or otherwise directs the subsidy, whether in-kind drug, cash, or a combination thereof, to the FNA Agent to fulfill the patient's request.

In other embodiments of the method 600 of FIG. 6, a D3PW can be included, e.g., perhaps under an agreement with the clearinghouse. The D3PW can be used to provide the requested drug, even if it is offered by a participating pharmaceutical provider. In such a case, the appropriate pharmaceutical provider can be required to replenish the D3PW's used stock. The D3PW can also be used to provide drugs of non-participating pharmaceutical providers, wherein payment for such drugs comes from at least some of the participating pharmaceutical providers, e.g., via clearinghouse 310.

Figure 7:
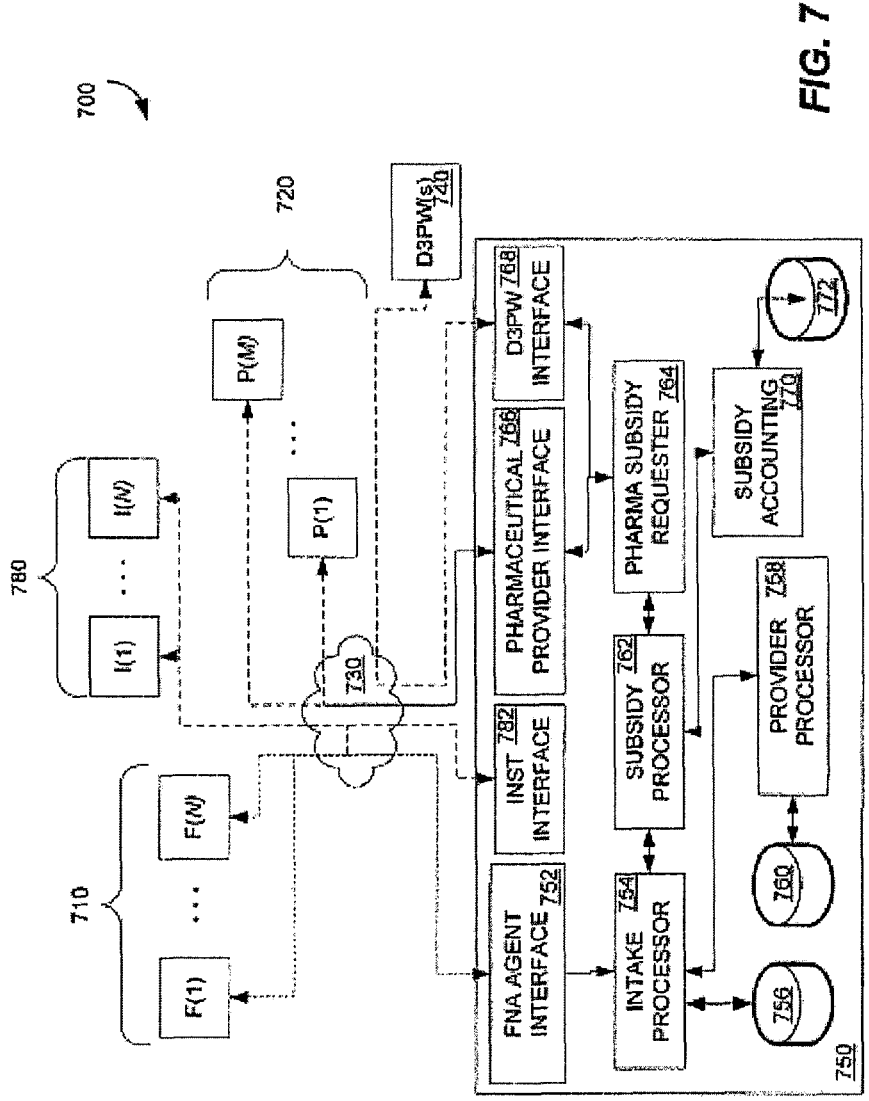
FIG. 7 is a block diagram example of a computer system that can be used to implement a clearinghouse method, such as that of FIG. 6.

FIG. 7 is a block diagram example of a computer system 700 that can be used to implement a clearinghouse method, such as that of FIG. 6. A clearinghouse system 750 is included that can be configured to work Inside Part D or Outside Part, or to host a combination of Inside Part D programs and Outside Part D functionality.

In this embodiment, block diagram 700 shows a set of FNA Agents F(1)-F(N) 710 that can register with clearinghouse system 750 on behalf of institutions I(1)-I(N) 780, for example. (Note "N" need not be the same in both cases.) FNA Agents 710 could thus become "in-network" FNA Agents. A set of pharmaceutical providers P(1)-P(M) 720 can also register with clearinghouse system 750, and become in-network pharmaceutical providers. The in-network FNA Agents 710 and the in-network pharmaceutical providers 720 can interact with clearinghouse system 750 over any of a variety of types of wired or wireless networks, or combinations thereof—collectively represented as network cloud 730. The networks may include the Internet, World Wide Web, local area networks, wide area networks, virtual private networks, or the like, and any combination thereof. At least one D3PW 740 can, optionally, be included as a source for disbursement of pharmaceuticals, under the guidance, control, supervision, and/or direction of clearinghouse system 750.

In various embodiments, clearinghouse system 750 may be implemented as a set of functional modules that can be implemented in hardware, software, firmware or some combination thereof. In this embodiment, an FNA Agent interface 752 facilitates interaction between the FNA Agents 710 and clearinghouse system 750, and can implement a set of login or security functionality for secure access by the registered FNA Agents 710. FNA Agent interface 752 also allows the submission of patient requests (e.g., approved applications) for a subsidy. The subsidy can be cash, in-kind drugs or a combination thereof, as examples. This may depend on whether of not the clearinghouse system is operating Inside Part D or Outside Part D. An intake processor 754 accesses a system database 756 that includes information about the in-network FNA Agents 710 and determines if the requesting FNA Agent is indeed registered as an in-network FNA Agent. If the FNA Agent is not a participating FNA Agent, then the intake processor can reject the request for a subsidy.

If the requesting FNA Agent is an in-network FNA Agent (i.e., a registered with clearinghouse 750) then the intake processor 754 tasks a provider processor 758 to determine the pharmaceutical provider that offers the requested drug—this can require checking a database 760 that includes a list of in-network pharmaceutical providers to see if one of them is the maker of the requested drug and/or accessing external databases and systems (not shown). The intake processor 754 then passes the request to a subsidy processor 762, along with an indication of the pharmaceutical provider of the requested drug, whether in-network or out-of-network.

If the requested drug is provided by an in-network pharmaceutical provider 720, then a pharma subsidy requester 764 prepares a request to the specific pharmaceutical provider to provide the subsidy. The subsidy processor 762 or pharma subsidy requester can determine or obtain the market value of that in-kind drug subsidy. However, if the requested drug is not provided by an in-network pharmaceutical provider 720, then the subsidy requester 764 determines the cost of the requested drug (which can be obtained from external sources) and determines the amount of cash contribution (or subsidy) due from each in-network pharmaceutical provider to procure the requested drug. The pharama subsidy requester 764 can also be configured to task the in-network pharmaceutical providers to contribute their respective portions of the subsidy, whether cash, in-kind drug, or a combination thereof. The pharama subsidy requester 764 can interact with the providers via a pharmaceutical provider interface 766 and network 730.

If the clearinghouse system 750 includes use of one or more D3PW 740, then a DP3W interface module 768 can be included. Via D3PW interface 768, D3PW 740 can be requested to supply the requested drug. If the drug is offered by an in-network pharmaceutical provider 720, then that pharmaceutical provider may be tasked to replenish the supply of the D3PW. In the requested drug is not provided by an in-network pharmaceutical provider 720, then D3PW 740 may still be tasked to provide the drug, with payment ultimately by one of more of the in-network pharmaceutical providers 720, as determined by clearinghouse system 750.

Similarly, institutions 780 could supply the drug from their bulk stock, with replenishment or payment as described above with respect to the D3PW. Accordingly, clearinghouse system 750 can also include an institution interface 782 for communicating with institutions 780 for such purposes or for other administrative purposes, such as for managing and verifying information related to at least one of the FNA Agents, institutions and PAPs, patients, and disbursements, as examples. Of course, the FNA Agents and institutions can, and presumably will in most embodiments, also communicate either via the clearinghouse system 750 or directly with each other, or both.

A subsidy accounting module 770 can be provided that stores and tracks the required subsidies to be made by each of the in-network providers 720 and can track which of the FNA Agents 710 received which subsidies. The subsidy accounting module 770 can also track the subsidies to each patient. It could also track the subsidies of each patient and the disbursements of the D3PWs 740 or institutions, if any. This information can be stored in accounting database 772. The subsidy accounting processor 770 can also track subsidy payments from the in-network pharmaceutical providers 720 against the amount they owe. The subsidy accounting processor 770 can also determine the totals and relative percentages of subsidies allocated to each in-network pharmaceutical provider and perform the tasks and calculations described with respect to FIGS. 4 and 5 above.

The clearinghouse system 750 can include modules for allowing or enabling on-line or electronic submission of patient requests by FNA Agents through a browser-based interface, as an example. Similarly, a browser-based interface can be provided for the in-network pharmaceutical providers, which can allow insight into financial information related to their subsidies, such as totals and percentage relative to all other in-network pharmaceutical providers. Clearinghouse system 750 can also include electronic payment of funds (or electronic funds transfer) functionality for enabling quick and efficient payment of subsidies by the in-network pharmaceutical providers, this could be implemented as part of subsidy accounting module 770. All of this could be implemented relative to specific disease states, or more generally.

The platforms used to host the above functional modules can be typically available personal computers, workstations, laptops, servers and the like. The system could be accessible by any of a variety of wired or wireless devices, or a combination thereof, including, but not limited to personal digital assistants and cellular telephones. The communications equipment, paths, interfaces, and protocols can be any appropriate in the prior art, so not discussed in detail herein.

In various embodiments, the clearinghouse can be implemented to provide all or some subsidies as free drug, as noted above. In the case of providing free drug, the clearinghouse can facilitate the acquisition on the open market of a drug offered by a non-participating pharmaceutical provider with the cash subsidies provided by the in-network pharmaceutical providers. In some embodiments, a portion (e.g., 25%) of the drugs of the in-network providers can also be acquired on the open market for purposes of, for example, establishing a price threshold for TrOOP valuations. The methods and systems described herein can also be adapted to use part cash and part drug for all pharmaceutical providers. And in-network pharmaceutical providers could be given the option of donating their drug when requested or donating a cash subsidy.

For lower cost drugs, the clearinghouse can work in a modified manner. For example, eligible patients can be provided universal coupons that can be applied against their drug costs and co-pays. The coupon will be valid for any drug in a given disease state. Disbursement agents can qualify patients using uniform criteria. The cost of couponing can be shared by in-network pharmaceutical providers, e.g., using the pro-rata share methodology, including the funding burden for out-of-network pharmaceutical providers.

While the foregoing has described what are considered to be the best mode and/or other preferred embodiments, it is understood that various modifications may be made therein and that the invention or inventions may be implemented in various forms and embodiments, and that they may be applied in numerous applications, only some of which have been described herein. For example, while the embodiments focus on pharmaceuticals, it could be implemented for any of a variety of patient therapies. As used herein, the terms "includes" and "including" mean without limitation. It is intended by the following claims to claim any and all modifications and variations that fall within the true scope of the inventive concepts.

What is claimed is:

1. A pharmaceutical clearinghouse method used for institutional patient assistance programs (PAPs), the method comprising:
    providing a clearinghouse computer system having a processor coupled to a data storage device and a network connection to enable communication with external computer systems over at least one network; and
    using the clearinghouse system processor and data storage device:
        defining in the data storage device a network of financial need assessment (FNA) Agents that process patients' requests for drugs under the institutional PAPs and a network of pharmaceutical providers that provide subsidies under the institutional PAPs, wherein the clearinghouse system processor applies a set of uniform criteria for enrolling FNA Agents into the network of FNA Agents;
        receiving an electronic patient request from an FNA agent for a drug within a given and defined disease state that has been prescribed to the patient by a physician and is provided by an institution under a PAP;
        electronically determining a subsidy required by each of the plurality of pharmaceutical providers to fill the patient request, wherein the subsidy can be cash, in-kind drug, or a combination thereof;
        matching the subsidy to the FNA Agent to fill the patient's request; and
        informing the pharmaceutical providers of their allocated share of needed subsidy, and then collecting and disbursing or otherwise directing the subsidy appropriately to the FNA Agent,
    wherein the requested drug may or may not be manufactured by the pharmaceutical providers,
    wherein each pharmaceutical provider in the network of pharmaceutical providers funds all patients that are prescribed the pharmaceutical provider's brand up to a predetermined limit,
    wherein each of the pharmaceutical providers also contributes an allocated share of cash funds to cover all other patients requesting drugs provided by non-participating pharmaceutical providers,
    wherein the burden of supporting a brand of drugs manufactured by non-participating pharmaceutical providers is shared by the participating pharmaceutical providers in a manner proportional to the benefit derived by the pharmaceutical provider in the form of its own drug subsidies through the clearinghouse relative to the other pharmaceutical participants,
    wherein the clearinghouse system does not electronically reveal an identity of the FNA agent to the plurality of pharmaceutical providers or an identity of the plurality of pharmaceutical providers to the FNA agent,
    wherein there is no data exchange between the clearinghouse and the pharmaceutical provider or between the foundations and pharmaceutical providers that allows pharmaceutical subsidy providers to correlate their donations to the number of prescriptions subsidized by a charity.

2. The method of claim 1, wherein the subsidy provided by a pharmaceutical provider can only be the drug identified in the patient request.

3. The method of claim 1, further comprising:
    the clearinghouse system electronically determining if the drug is available from an in-network pharmaceutical provider.

4. The method of claim 3, wherein if the drug is available from an in-network pharmaceutical provider, the method including:
    the in-network pharmaceutical provider providing the subsidy in the form of only the drug; and
    the clearinghouse system storing the drug name and amount in association with the in-network pharmaceutical provider.

5. The method of claim 3, wherein if the drug is available from an in-network pharmaceutical provider, the method including:
    the in-network pharmaceutical provider providing the subsidy in the form of the drug and cash; and
    the clearinghouse system storing the drug name and amount of cash in association with the in-network pharmaceutical provider.

6. The method of claim 3, wherein if the drug is available from an in-network pharmaceutical provider, the method including the clearinghouse system:
    storing a fair market value of the drug;
    determining the subsidy to include a cash amount based on the fair market value of the drug;
    requesting the cash amount from the in-network pharmaceutical provider;
    generating an order for the drug at the fair market value; and
    applying the cash amount to the order to procure the drug on the open market.

7. The method of claim 3, wherein if the drug is not available from any in-network pharmaceutical provider, the method including:
    the clearinghouse system determining a cash amount needed to procure the drug; and
    the clearinghouse system determining a cash portion of the cash amount to be paid by one or more of the in-network pharmaceutical providers.

8. The method of claim 7, wherein determining the cash portion includes determining a pro rata portion to be paid by each of the in-network pharmaceutical providers, including determining the pro rata portion as a function of the total amount of all subsidies provided by the in-network pharmaceutical providers.

9. The method of claim 1, including:
    the clearinghouse system receiving the patient request as a single application and a plurality of FNA Agents processing the application to generate competitive offers to obtain the subsidy and provide the drug.

10. The method of claim 1, further comprising:
    the clearinghouse system establishing in the pharmaceutical provider database a low-cost pharmaceutical provider threshold, whereby in-network pharmaceutical providers that provide drugs that cost less than the low-cost threshold do not subsidize in-network pharmaceutical providers having drugs that cost more than the low cost threshold.

11. The method of claim 1, further comprising:
the clearinghouse system establishing in the pharmaceutical provider database a low-cost pharmaceutical provider threshold, whereby in-network pharmaceutical providers that provide drugs that cost less than the low-cost threshold provide subsidies in a smaller proportion than the in-network pharmaceutical providers having drugs that cost more than the low cost threshold.

12. The method of claim 1, further comprising:
the clearinghouse system defining in a memory a uniform and auditable standard of patient need assessment; and
determining an eligibility of the patient for the subsidy by electronically applying the uniform and auditable standard of patient need assessment to the patient request.

13. The method of claim 1, further comprising:
providing the subsidy in the form of one or more coupons that can be applied against the drug costs and patient co-pay for any drug in a given disease state.

14. The method of claim 1, further comprising:
the clearinghouse system electronically generating an order for obtaining the subsidy from a designated third party wholesaler.

15. The method of claim 1, further comprising:
the clearinghouse system electronically generating an order for obtaining the subsidy from an institution represented by the FNA Agent.

16. A pharmaceutical clearinghouse system for institutional patient assistance programs (PAPs), the clearinghouse system comprising:
a processor coupled to a memory system, a network connection to enable communication with external computer systems over at least one network, and a set of computer program modules stored in the memory device and executable by the processor to perform a clearinghouse method comprising:
a set of FNA Agent modules configured to define in the memory system a network of financial need assessment (FNA) Agents that process patients' requests for drugs under the institutional PAPs, which applies a set of uniform criteria to enroll FNA Agents into the network of FNA Agents;
a set of pharmaceutical provider modules configured to define in the memory system a network of pharmaceutical providers that provide subsidies under the institutional PAPs; and
a set of subsidy module configured to receive an electronic patient request from an FNA agent for a drug within a given and defined disease state provided by an institution under a PAP on behalf of a patient who has been prescribed that drug by a physician, electronically determine a subsidy required by each of the plurality of pharmaceutical providers to fill the patient request, wherein the subsidy can be cash, in-kind drug, or a combination thereof, and match the subsidy to the FNA Agent to fill the patient's request, inform the pharmaceutical providers of their allocated share of needed subsidy, and then collect and disburse or otherwise direct the subsidy appropriately to the FNA Agent,
wherein the requested drug may or may not be manufactured by the pharmaceutical providers,
wherein each pharmaceutical provider in the network of pharmaceutical providers funds all patients that are prescribed the pharmaceutical provider's brand up to a predetermined limit,
wherein each of the pharmaceutical providers also contributes an allocated share of cash funds to cover all other patients requesting drugs provided by non-participating pharmaceutical providers,
wherein the burden of supporting a brand of drugs manufactured by non-participating pharmaceutical providers is shared by the participating pharmaceutical providers in a manner proportional to the benefit derived by the pharmaceutical provider in the form of its own drug subsidies through the clearinghouse relative to the other pharmaceutical participants, and
wherein the clearinghouse system does not electronically reveal an identity of the FNA agent to the plurality of pharmaceutical providers or an identity of the plurality of pharmaceutical providers to the FNA agent, and
wherein there is no data exchange between the clearinghouse and the pharmaceutical provider or between the foundations and pharmaceutical providers that allows pharmaceutical subsidy providers to correlate their donations to the number of prescriptions subsidized by a charity.

17. The system of claim 16, wherein the subsidy provided by a pharmaceutical provider can only be the drug identified in the patient request.

18. The system of claim 16, wherein the set of subsidy modules is configured to determine if the drug is available from an in-network pharmaceutical provider.

19. The system of claim 17, wherein if the drug is available from the in-network pharmaceutical provider, the set of subsidy modules is configured to:
request the subsidy from the in-network pharmaceutical provider in the form of only the drug; and
store the drug name and amount in association with the in-network pharmaceutical provider.

20. The system of claim 17, wherein if the drug is available from the in-network pharmaceutical provider, the set of subsidy modules is configured to:
request the subsidy from the in-network pharmaceutical provider in the form of the drug and cash; and
store the drug name and an amount of cash in association with pharmaceutical provider.

21. The system of claim 17, wherein if the drug is available from the in-network pharmaceutical provider, the set of subsidy modules is configured to:
store a fair market value of the drug;
determine the subsidy to include a cash amount based on the fair market value of the drug;
request the cash amount from the in-network pharmaceutical provider;
generate an order for the drug at the fair market value; and
apply the cash amount to the order to procure the drug.

22. The system of claim 17, wherein if the drug is not available from at least one in-network pharmaceutical provider, the set of subsidy modules is configured to:
determine a cash amount needed to procure the drug; and
determine a cash portion of the cash amount to be paid by one or more of the in-network pharmaceutical providers.

23. The system of claim 22, wherein the set of subsidy modules is configured to determine a pro rata portion of the cash portion to be paid by each of the one or more in-network pharmaceutical providers, as a function of the total amount of all subsidies provided by the in-network pharmaceutical providers.

24. The system of claim 16, wherein the clearinghouse system is configured to make the patient request accessible by a plurality of the in-network FNA Agents to enable the plurality of in-network FNA Agents to generate competitive offers to obtain the subsidy and provide the drug.

25. The system of claim 16, wherein the clearinghouse system is configured to establish a low-cost pharmaceutical provider threshold, and the set of subsidy modules is configured to determine the subsidy such that in-network pharmaceutical providers that provide drugs that cost less than the low-cost threshold do not subsidize in-network pharmaceutical providers having drugs that cost more than the low cost threshold.

26. The system of claim 16, wherein the clearinghouse system is configured to establish a low-cost pharmaceutical provider threshold, and the set of subsidy modules is configured to determine the subsidy such that in-network pharmaceutical providers that provide drugs that cost less than the low-cost threshold provide subsidies in a smaller proportion than in-network pharmaceutical providers having drugs that cost more than the low cost threshold.

27. The system of claim 16, wherein the clearinghouse system is configured to:
   define in the memory system a uniform and auditable standard of patient need assessment; and
   determine an eligibility of the patient for the subsidy by electronically applying the uniform and auditable standard of patient need assessment to the patient request.

28. The system of claim 16, wherein the clearinghouse is configured to generate the subsidy in the form of one or more coupons that can be applied against the drug costs and patient co-pay for any drug in a given disease state.

29. The system of claim 16, wherein the set of subsidy modules is configured to generate an order for obtaining the subsidy from a designated third party wholesaler.

30. The system of claim 16, wherein the set of subsidy modules is configured to electronically generate an order for obtaining the subsidy from an institution represented by the FNA Agent.

* * * * *